(12) United States Patent
Rogan

(10) Patent No.: US 10,334,884 B2
(45) Date of Patent: Jul. 2, 2019

(54) AEROSOL GUIDING DEVICE AND AEROSOL GENERATING SYSTEM COMPRISING SAID AEROSOL GUIDING DEVICE

(71) Applicant: JT International S.A., Geneva (CH)

(72) Inventor: Andrew Robert John Rogan, Forres (GB)

(73) Assignee: JT International S.A. (CH)

( * ) Notice: Subject to any disclaimer, the term of this patent is extended or adjusted under 35 U.S.C. 154(b) by 11 days.

(21) Appl. No.: 15/548,677

(22) PCT Filed: Feb. 5, 2016

(86) PCT No.: PCT/EP2016/052505
§ 371 (c)(1),
(2) Date: Aug. 3, 2017

(87) PCT Pub. No.: WO2016/124740
PCT Pub. Date: Aug. 11, 2016

(65) Prior Publication Data
US 2018/0000159 A1 Jan. 4, 2018

(30) Foreign Application Priority Data
Feb. 5, 2015 (GB) .................... 1501951.6

(51) Int. Cl.
*A24F 13/00* (2006.01)
*A24F 47/00* (2006.01)
(Continued)

(52) U.S. Cl.
CPC .............. *A24F 47/008* (2013.01); *F22B 1/28* (2013.01); *H05B 6/108* (2013.01)

(58) Field of Classification Search
CPC ...................................................... A24F 47/008
(Continued)

(56) References Cited

U.S. PATENT DOCUMENTS 10,051,892 B2 8/2018 Rogan et al.
2004/0187868 A1 9/2004 Hochrainer et al.
(Continued)

FOREIGN PATENT DOCUMENTS

| DE | 102005010965 B3 | 8/2006 |
|---|---|---|
| EP | 2319334 A1 | 5/2011 |
| EP | 2754361 A1 | 7/2014 |

OTHER PUBLICATIONS

International Search Report for Application No. PCT/EP2016/052505 dated Mar. 29, 2016.
(Continued)

*Primary Examiner* — Phuong K Dinh
(74) *Attorney, Agent, or Firm* — Lerner, David, Littenberg, Krumholz & Mentlik, LLP

(57) ABSTRACT

An aerosol generating system may include aerosol generating means, aerosol delivery means, and an aerosol guiding device. The aerosol guiding device may include a chamber having an air inlet and an air outlet, and the aerosol delivery means may be configured such that aerosol is introduced from the aerosol generating means into the chamber in use. An airflow route may be defined from the air inlet to the air outlet so as to convey the aerosol to the air outlet, and the relative dimensions of the air inlet and the air outlet may be selected to provide pressure control means for controlling the pressure differential between the air inlet and the air outlet. An aerosol guiding device for use in an aerosol generating system may include a chamber having an air inlet and an air outlet.

17 Claims, 4 Drawing Sheets

(51) Int. Cl.
*F22B 1/28* (2006.01)
*H05B 6/10* (2006.01)

(58) Field of Classification Search
USPC .................................................. 131/328–329
See application file for complete search history.

(56) References Cited

U.S. PATENT DOCUMENTS

| | | |
|---|---|---|
| 2013/0152922 A1 | 6/2013 | Benassayag et al. |
| 2013/0333709 A1 | 12/2013 | Shimizu |
| 2014/0069444 A1 | 3/2014 | Cyphert et al. |
| 2015/0090278 A1* | 4/2015 | Schiff .................. A24F 47/008 131/328 |
| 2016/0081395 A1* | 3/2016 | Thorens ................ A24F 47/008 128/202.21 |
| 2016/0235121 A1 | 8/2016 | Rogan et al. |
| 2018/0000159 A1 | 1/2018 | Rogan |
| 2018/0014574 A1 | 1/2018 | Rogan |
| 2018/0220708 A1 | 8/2018 | Scott et al. |

OTHER PUBLICATIONS

International Search Report for Application No. PCT/EP2016/052506 dated Apr. 5, 2016.

* cited by examiner

AEROSOL GUIDING DEVICE AND AEROSOL GENERATING SYSTEM COMPRISING SAID AEROSOL GUIDING DEVICE

CROSS-REFERENCE TO RELATED APPLICATIONS

The present application is a national phase entry under 35 U.S.C. § 371 of International Application No. PCT/EP2016/052505, filed Feb. 5, 2016, published in English, which claims priority from United Kingdom Application No. 1501951.6, filed Feb. 5, 2015, all of which are incorporated herein by reference.

BACKGROUND OF THE INVENTION

The present invention relates to an aerosol guiding device and an aerosol generating system containing said aerosol guiding device. More particularly, it relates to an aerosol guiding device for controlling and modifying air flow for use in an aerosol generating system such as an electronic cigarette.

Aerosol generating systems such as electronic cigarettes are becoming well known in the art. The operating principle for these electronic cigarettes usually centres around providing a flavoured vapour to a user without burning material. Some known devices comprise a capillary wick and a coil heater, which can be activated by the user through suction on a mouthpiece of the device, or by for example activating a push button on the device. This switches on a battery power supply that activates the heater, which vaporises a liquid or solid material. Suction on the mouthpiece further causes air to be drawn into the device through one or more air inlets and towards the mouthpiece via the capillary wick, and the vapour that is produced near the capillary wick mixes with air from the air inlet and is conveyed towards the mouthpiece as an aerosol.

An important factor in the design of aerosol generating systems such as electronic cigarettes is the regulation of air flow within the system, which impacts upon the quality and quantity of aerosol delivered to the user. Particle size of the aerosol is also an important consideration, and optimum particle size of the aerosol may be determined for optimum delivery of said aerosol to the lungs; aerosol particles that have diameter greater than for example 1.0 micrometer may be trapped or obstructed before they reach the lungs, and aerosol particles having diameter for example smaller than 1.0 micrometer may be delivered more effectively to the lungs.

Some attempts have been made to address the above problems. For example, with the device of EP2319334A1, air flow speed may be controlled within the device by varying the cross sectional area of the air flow route upstream of the capillary wick so as to take advantage of the Venturi effect. Air flow through a constricted section increases in speed in order to satisfy the principle of continuity, while its pressure must decrease in order to conserve mechanical energy. Similarly, air flow through a wider section must conversely decrease in speed, whilst its pressure increases.

A problem with known devices that attempt to control air flow speed, however, is that inconsistencies within the system, for example due to manufacturing tolerances, or inconsistencies due to external factors, for example varied suction of a user, may lead to a consequent variance in the resultant air flow within the aerosol generating system. For example, the pressure drop in vaporisation chambers of current models of electronic cigarettes sometimes varies widely between 40 mmWC and 250 mmWC, and more commonly between 100 mmWC and 125 mmWC. In addition, there are often significant inconsistencies in the pressure drop achieved in vaporisation chambers used across electronic cigarettes of the same model. A further problem is that if these inconsistences arise in a particular design of electronic cigarette, it is almost impossible to then change that design in order to further modify air flow, thus resulting in lack a flexibility of the entire system.

Due to the inconsistency in pressure drop within current aerosol generating systems, it is possible that no liquid or solid material to be vaporised may be present on the wick when a user provides suction action on the mouthpiece. This leads to an unpleasant effect called "dry puffing" where the capillary wick is burnt by the heater and a burnt taste is experienced by the user. In other cases, too much liquid or solid material may be present on the capillary wick, in which case the heater cannot vaporise all of said material, thus resulting in an inefficient system.

BRIEF SUMMARY OF THE INVENTION

The present invention seeks to provide an aerosol generating system such as an electronic cigarette which overcomes the abovementioned problems, including providing flexible and improved means for modifying and regulating air flow within the aerosol generating system.

The present inventors have recognised that a greater degree of flexibility and control is required to enhance the smoking experience of an aerosol generating system such as an electronic cigarette.

Accordingly, viewed from one aspect of the present invention, there is provided an aerosol generating system, the system comprising: aerosol generating means; aerosol delivery means; and an aerosol guiding device, wherein the aerosol guiding device comprises a chamber having an air inlet and an air outlet, the aerosol delivery means being configured such that aerosol is introduced from the aerosol generating means into the chamber in use, wherein an air flow route is defined from the air inlet to the air outlet so as to convey the aerosol to the air outlet, and wherein the relative dimensions of the air inlet and the air outlet are selected to provide pressure control means for controlling the pressure differential between the air inlet and the air outlet.

In use, when the system is activated, the aerosol generating means vaporises liquid material to form a supersaturated vapour (or in the case of a solid material, the aerosol generating means causes sublimation such that the supersaturated vapour is formed from the solid material) which mixes with air from at least one air inlet and condenses to form an aerosol, which is delivered to the chamber of the aerosol guiding device via aerosol delivery means. By action of suction of the mouth of a user, the aerosol is conveyed towards the air outlet of the chamber of the aerosol guiding device such that an air flow route is defined from the air inlet to the air outlet of the chamber in a direction from an upstream portion of the chamber to a downstream portion of the chamber.

In the present invention, the term "aerosol generating means" should be understood to denote any means by which aerosol may be generated. For example, the aerosol generating means may comprise a heater, or a heater and wick assembly, as will be described below. In other example, the aerosol generating means may comprise a pressure drop control means for reducing the boiling point of a liquid or sublimation point of a solid, for example, by virtue of the shape of the chamber. In yet another example, the aerosol generating means may comprise an aerosol spray system, a nebuliser, electrospray apparatus and/or an vibrating orifice aerosol generator, just to name a few.

In the present invention, the term "aerosol delivery means" should be understood to denote any means for ensuring that aerosol which is generated by the aerosol generating means is delivered to the chamber in use. For example, the aerosol delivery means may comprise at least one piercing through the wall of the chamber for example, for receiving a wick such that aerosol is generated within (and delivered to) the chamber in use. Additionally or alternatively, the aerosol delivery means may comprise a tube for guiding the aerosol into and towards the chamber from an aerosol generating means that is positioned outside of the chamber in use. Alternatively, the aerosol delivery means may comprise a directing means for directing aerosol to the chamber such as a directing component, for example, a guide, and/or means to provide an orientation of the aerosol generating means such that aerosol is directed towards the chamber, for example, using positioning means.

The aerosol generating system according to the present invention, which may be an electronic cigarette, provides a number of advantages. Significantly, the relative dimensions of the air inlet and the air outlet is selected to provide pressure control means for controlling the pressure differential between the air inlet and the air outlet of the chamber of the aerosol guiding device. In particular, the relative dimensions of the air inlet and the air outlet may also impact on the air flow speed and intensity within the chamber. The relative tapering of the upstream and downstream portions of the chamber may further provide pressure control means.

The air inlet and the air outlet of the chamber may be of the same dimensions. In this case, the pressure differential between said air inlet and said air outlet may be zero.

The air inlet may have larger dimensions than the air outlet. In this case, there may be an overall pressure drop across the chamber of the aerosol guiding device.

The air inlet may have smaller dimensions than the air outlet. In this case, there may be an overall pressure increase across the chamber of the aerosol guiding device.

Preferably, the chamber of the aerosol guiding device may comprise a constricted section such that an upstream portion of the chamber is defined between the air inlet and the constricted section and a downstream portion of the chamber is defined between the constricted section and the air outlet. Said constricted section may be the narrowest part of the chamber.

In this case, aerosol may be introduced into the aerosol guiding device by the aerosol delivery means at the constricted section, which may also be the narrowest part of the chamber, where an area of low pressure exists as a result of the vacuum effect. In some preferred examples, aerosol may be generated at the narrowest part of the chamber in use. In the case where the material to be vaporised is a liquid, the area of low pressure at the narrowest part of the chamber draws liquid in and at the same time the configuration of the narrowest part of the chamber increases air flow speed by virtue of the Venturi effect. In the case of a solid material to be vaporised (or sublimed), the aerosol delivery means may be configured to position said solid material in close proximity to the narrowest part of the chamber and in close proximity to the aerosol generating means such that the solid material is vaporised (or sublimed) and delivered to the narrowest part of the chamber in use, the point at which air flow speed is increased by virtue of the Venturi effect.

In this example, the narrowest part of the chamber is also the point at which air flow through the aerosol guiding means is fastest. By controlling the size and configuration of the narrowest part of the chamber, both air flow speed and air flow direction are regulated, and particle size in the resulting aerosol is controlled and in particular reduced relative to known devices. Furthermore, the faster the flow of air is in the air flow route in use, the more aerosol can be delivered to the user per puff, thus resulting in a more effective aerosol delivery mechanism and improving both efficiency of the system and the smoking experience for the user.

In the case where the material to be vaporised is a liquid, the liquid may be stored within a liquid reservoir either inside or outside of the chamber of the aerosol guiding device. The configuration of such a liquid reservoir will be described in further detail below. The liquid to be vaporised may have physical properties that are suitable for use in the aerosol generating system of the present invention, for example, it may have a boiling point that is suitable for vaporising said liquid at the narrowest part of the chamber. If the boiling point of the liquid is too high, then the aerosol generating means will not be able to vaporise said liquid. If the boiling point of the liquid is too low, the liquid may be vaporised even before the aerosol generating means is activated.

The use of a liquid material to be vaporised delivers particular advantages in combination with the delivery of aerosol at the narrowest part of the chamber. For example, the area of reduced air pressure at the narrowest point lowers the boiling point of such a liquid, thus making the device more efficient and saving electrical power. The narrowest part of the chamber may therefore be the aerosol generating means by virtue of its shape. Further, the reduced pressure at the narrowest part of the chamber acts to draw liquid from the liquid reservoir towards the narrowest part of the chamber, resulting in better puff-to-puff consistency and ensuring that there is always sufficient liquid to be vaporised, which eliminates the problem of dry puffing. This also results in an increased flow rate of aerosol through the aerosol generating system, which will enhance the user experience by providing an increase in aerosol production per puff.

The liquid material preferably comprises tobacco or flavourants comprising tobacco. In addition or alternatively, the liquid material may comprise flavourants not comprising tobacco. The liquid may further comprise glycerine or glycol derivatives or a mixture thereof.

Preferably, the upstream portion of the chamber and the downstream portion of the chamber may taper from the air inlet and the air outlet respectively towards the constricted section. The tapering of the chamber advantageously provides improved control of the pressure differential along the air flow route. In particular, the gradual gradients of the tapered portion(s) reduce drag in the chamber and thus regulate air flow in a controlled manner.

Preferably, the taper angle of the upstream portion of the chamber may be larger than the taper angle of the downstream portion of the chamber and/or the length of the upstream portion of the chamber may be smaller than the length of the downstream portion of the chamber.

Alternatively, the chamber of the aerosol guiding device may comprise an upstream portion that tapers inwardly from the air inlet. In addition or alternatively, the chamber of the aerosol guiding device may comprise a downstream portion that tapers inwardly from the air outlet.

In each of the examples of the present invention comprising tapering, the taper angle of the upstream portion of the chamber may be between 20 and 40 degrees relative to the longitudinal axis of the chamber, more preferably between 25 and 35 degrees, and yet more preferably 30 degrees. Further, the taper angle of the downstream portion of the chamber may be between 3 and 7 degrees relative to the longitudinal axis of the chamber, more preferably between 4 and 6 degrees, and yet more preferably 5 degrees. These particular taper angles have been identified by the present inventors to provide an optimum increase in air flow rate in the chamber whilst maintaining a suitable pressure differential across the chamber of the aerosol guiding device in use.

Typical preferred dimensions of the aerosol guiding device may be between 14 and 15 millimeters in length, 10 to 15 millimeters in diameter at the widest part, and 1 to 5 millimeters at its narrowest part, wherein the length of the upstream portion may be between 8 and 10 millimeters, and the length of the downstream portion may be between 30 and 40 millimeters. In a specific example, the length of the aerosol guiding device may be 46.5 millimeters in total, the diameter at its widest part may be 13.5 millimeters, the diameter at its narrowest part may be 2 millimeters, the length of the upstream portion may be 9.25 millimeters, and the length of the downstream portion may be 37.25 millimeters. These particular dimensions of the aerosol guiding device preferably allow it to sit comfortably within an aerosol guiding system in order that air flow may be regulated and optimised through the device.

In another example, the chamber of the aerosol guiding device may comprise at least two constricted sections. Said at least two constricted sections may be of the same size, length and/or shape. At least two constricted sections are of the same size, then both or each of said at least two constricted sections may represent the narrowest parts of the chamber. Alternatively, the at least two constricted sections may be of different size, length and/or shape.

Preferably, the aerosol guiding device comprises a circular cross sectional shape. Viewed from a plane orthogonal to the cross sectional area, the diameter of the circular or any other shape of cross sectional area of the chamber may decrease or increase across the length of said chamber.

The shape of the chamber of the aerosol guiding device may provide further pressure control means. For example, the tapering of the walls of the chamber may provide further pressure control means in addition to that provided by the relative dimensions of the air inlet and the air outlet of the chamber. For example, the gradual gradients of the tapered walls of the chamber may act to reduce drag and therefore homogenise the pressure across a particular cross section of the chamber.

Preferably, the pressure control means may be configured to provide a pressure differential between the air inlet and the air outlet of the chamber of between 75 and 110 mmWC in use. The pressure differential may preferably be a pressure drop. This range of pressure drop across the chamber is the pressure drop across the length of a conventional cigarette.

The aerosol guiding device preferably comprises thermally insulating material, for example plastic. Of course, other thermally insulating materials may be contemplated, and in particular, according to the nature of the aerosol that will be generated by the aerosol generating means and such materials are known to those skilled in the art. One advantage of this is the reduced heat loss within the aerosol guiding device so that the thermal efficiency of the aerosol generating system may be improved. This is of particular importance if the aerosol generating means comprises a heater.

The chamber of the aerosol guiding device may be ribbed internally. Such a configuration may advantageously reduce the amount of sheath flow of air along the walls of the chamber, thus improving efficiency of the system.

The chamber of the aerosol guiding device may preferably be manufactured using 3D printing technologies. The chamber may also preferably comprise a single body element which acts to reduce inter component variability. The use of a single element also avoids the need to assemble multiple components, thus increasing the ease of use of the device. This is especially advantageous if for example the chamber is faulty or has reached the end of its lifetime and is no longer working as the present invention allows it to be replaced quickly and easily.

Various positions of the aerosol guiding device within the aerosol generating system may be contemplated. In one example, the aerosol generating system may further comprise an outer shell for housing the chamber of the aerosol guiding device. The outer shell may be configured to receive the aerosol guiding device, which may be insertable and removable from the aerosol generating system. This provides a particular advantage in that different aerosol guiding devices may be provided for the aerosol generating system dependent upon various operational factors. The insertable and removable nature of the aerosol guiding device is also advantageous in that said device may be changed should the operational circumstances of the aerosol generating system change over time. The aerosol guiding device may further comprises securing means that secures it to the outer shell of the aerosol generating system, for example, an O-ring, which prevents undesired movement of the aerosol guiding device within the aerosol generating system in use. The aerosol guiding device may further provide structural integrity to the aerosol generating system.

Preferably, the aerosol generating means of the aerosol generating system may be located outside the aerosol guiding device and/or in close proximity to a narrowest part of the chamber. Alternatively, the aerosol generating means of the aerosol generating system may be located inside the aerosol guiding device. An advantage of locating the aerosol generating means outside the aerosol guiding device is that it will not impact or modify air flow in the chamber of the aerosol guiding device. However, if the aerosol generating means is located inside the aerosol guiding device, then it may be configured to further regulate air flow in the air flow route by acting as a guide around which the air must flow. In this example, the aerosol generating means may also act as a trap component for trapping aerosol particles having a diameter greater than about 1.0 micrometer. This not only removes the aerosol particles that may not reach the lungs of a user anyhow, but it also acts to provide better uniformity to the particle size of aerosol particles by removing said aerosol particles.

Preferably, the aerosol generating means may comprise a heater, wherein the heater comprises any one of a ceramic, a coil of wire, inductive heating means, ultrasonic heating means and/or piezoelectric heating means.

Preferably, the aerosol generating means may further comprise a wick that is received by the chamber of the aerosol guiding device and the wick may be in communication with a liquid reservoir. The aerosol generating system may further comprise said liquid reservoir. The wick may be received by the chamber at its narrowest part through at least one piecing.

In one example, the aerosol generating means may further comprise a wick that is received by the chamber of the aerosol guiding device at its narrowest part through at least one piecing and the wick may be in communication with a liquid reservoir. In this example, the aerosol generating means may comprise a coil heater, said coil heater being located at the narrowest part of the chamber or substantially at the narrowest part of the chamber. The wick may draw liquid to be vaporised from at least one liquid reservoir located outside of the chamber of the aerosol guiding device, for example.

Viewed from another aspect of the present invention, there is provided an aerosol guiding device for use in an aerosol generating system, the device comprising: a chamber having an air inlet and an air outlet; wherein aerosol is introduced from an aerosol generating means into the chamber in use, wherein an airflow route is defined from the air inlet to the air outlet so as to convey the aerosol to the air outlet, and wherein the relative dimensions of the air inlet and the air outlet are selected to provide pressure control means for controlling the pressure differential between the air inlet and the air outlet. The aerosol generating system may be an electronic cigarette.

It will be appreciated that all of the features and advantages associated with the aerosol guiding device of the aerosol generating system described above may equally apply to the aerosol guiding device alone.

The air inlet and the air outlet of the chamber may be of the same dimensions. In this case, the pressure differential between said air inlet and said air outlet may be zero.

The air inlet may have larger dimensions than the air outlet. In this case, there may be an overall pressure drop across the chamber of the aerosol guiding device.

The air inlet may have smaller dimensions than the air outlet. In this case, there may be an overall pressure increase across the chamber of the aerosol guiding device.

Preferably, the chamber of the aerosol guiding device may comprise a constricted section such that an upstream portion of the chamber is defined between the air inlet and the constricted section and a downstream portion of the chamber is defined between the constricted section and the air outlet. Said constricted section may be the narrowest part of the chamber.

Preferably, the upstream portion of the chamber and the downstream portion of the chamber may taper from the air inlet and the air outlet respectively towards the constricted section. The tapering of the chamber advantageously provides improved control of the pressure differential along the air flow route. In particular, the gradual gradients of the tapered portion(s) reduce drag in the chamber and thus regulate air flow in a controlled manner.

Preferably, the taper angle of the upstream portion of the chamber may be larger than the taper angle of the downstream portion of the chamber and/or the length of the upstream portion of the chamber may be smaller than the length of the downstream portion of the chamber.

Alternatively, the chamber of the aerosol guiding device may comprise an upstream portion that tapers inwardly from the air inlet. In addition or alternatively, the chamber of the aerosol guiding device may comprise a downstream portion that tapers inwardly from the air outlet.

In each of the examples of the present invention comprising tapering, the taper angle of the upstream portion of the chamber may be between 20 and 40 degrees relative to the longitudinal axis of the chamber, more preferably between 25 and 35 degrees, and yet more preferably 30 degrees. Further, the taper angle of the downstream portion of the chamber may be between 3 and 7 degrees relative to the longitudinal axis of the chamber, more preferably between 4 and 6 degrees, and yet more preferably 5 degrees. These particular taper angles have been identified by the present inventors to provide an optimum increase in air flow rate in the chamber whilst maintaining a suitable pressure differential across the chamber of the aerosol guiding device in use.

Typical preferred dimensions of the aerosol guiding device may be between 14 and 15 millimeters in length, 10 to 15 millimeters in diameter at the widest part, and 1 to 5 millimeters at its narrowest part, wherein the length of the upstream portion may be between 8 and 10 millimeters, and the length of the downstream portion may be between 30 and 40 millimeters. In a specific example, the length of the aerosol guiding device may be 46.5 millimeters in total, the diameter at its widest part may be 13.5 millimeters, the diameter at its narrowest part may be 2 millimeters, the length of the upstream portion may be 9.25 millimeters, and the length of the downstream portion may be 37.25 millimeters. These particular dimensions of the aerosol guiding device preferably allow it to sit comfortably within an aerosol guiding system in order that air flow may be regulated and optimised through the device.

In another example, the chamber of the aerosol guiding device may comprise at least two constricted sections. Said at least two constricted sections may be of the same size, length and/or shape. At least two constricted sections are of the same size, then both or each of said at least two constricted sections may represent the narrowest parts of the chamber. Alternatively, the at least two constricted sections may be of different size, length and/or shape.

Preferably, the aerosol guiding device comprises a circular cross sectional shape. Viewed from a plane orthogonal to the cross sectional area, the diameter of the circular or any other shape of cross sectional area of the chamber may decrease or increase across the length of said chamber.

The shape of the chamber of the aerosol guiding device may provide further pressure control means. For example, the tapering of the walls of the chamber may provide further pressure control means in addition to that provided by the relative dimensions of the air inlet and the air outlet of the chamber. For example, the gradual gradients of the tapered walls of the chamber may act to reduce drag and therefore homogenise the pressure across a particular cross section of the chamber.

Preferably, the pressure control means may be configured to provide a pressure differential between the air inlet and the air outlet of the chamber of between 75 and 110 mmWC in use. The pressure differential may preferably be a pressure drop. This range of pressure drop across the chamber is the pressure drop across the length of a conventional cigarette.

The aerosol guiding device preferably comprises thermally insulating material, for example plastic. Of course, other thermally insulating materials may be contemplated, and in particular, according to the nature of the aerosol that will be generated by the aerosol generating means and such materials are known to those skilled in the art. One advantage of this is the reduced heat loss within the aerosol guiding device so that its thermal efficiency may be improved. This is of particular importance if the aerosol generating means comprises a heater.

The chamber of the aerosol guiding device may be ribbed internally. Such a configuration may advantageously reduce the amount of sheath flow of air along the walls of the chamber, thus improving efficiency of the device.

The chamber of the aerosol guiding device may preferably be manufactured using 3D printing technologies. The chamber may also preferably comprise a single body element which acts to reduce inter component variability. The use of a single element also avoids the need to assemble multiple components, thus increasing the ease of use of the device. This is especially advantageous if for example the chamber is faulty or has reached the end of its lifetime and is no longer working as the present invention allows it to be replaced quickly and easily.

Preferably, the aerosol guiding device may be insertable and removable from an aerosol generating system. This provides a particular advantage in that different aerosol guiding devices may be provided for an aerosol generating system dependent upon various operational factors. The insertable and removable nature of the aerosol guiding device is also advantageous in that said device may be changed should the operational circumstances of the aerosol generating system change over time. The aerosol guiding device may further comprises securing means that secures if to the outer shell of the aerosol generating system, for example, an O-ring, which prevents undesired movement of the aerosol guiding device within the aerosol generating system in use. The aerosol guiding device may further provide structural integrity to an aerosol generating system.

BRIEF DESCRIPTION OF THE DRAWINGS

Certain preferred embodiments of the present invention will now be described by way of example only with reference to the accompanying drawings, in which.

DETAILED DESCRIPTION

Figure 1A:
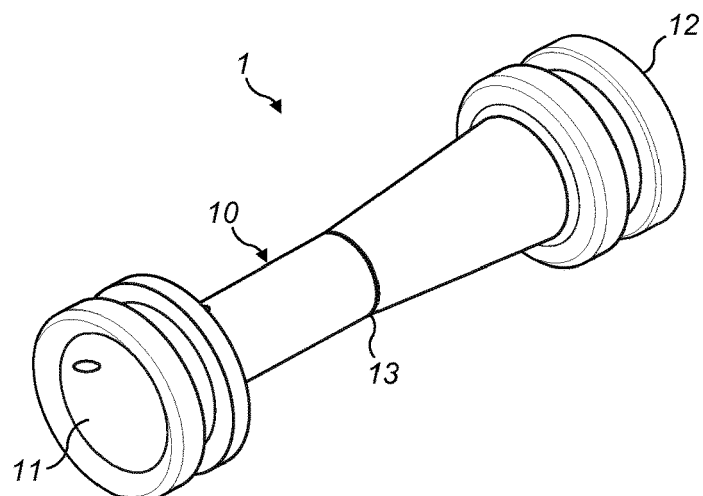
FIGS. 1A to 1C show schematic representations of an aerosol guiding device according to an embodiment of the present invention.
Figure 1B:
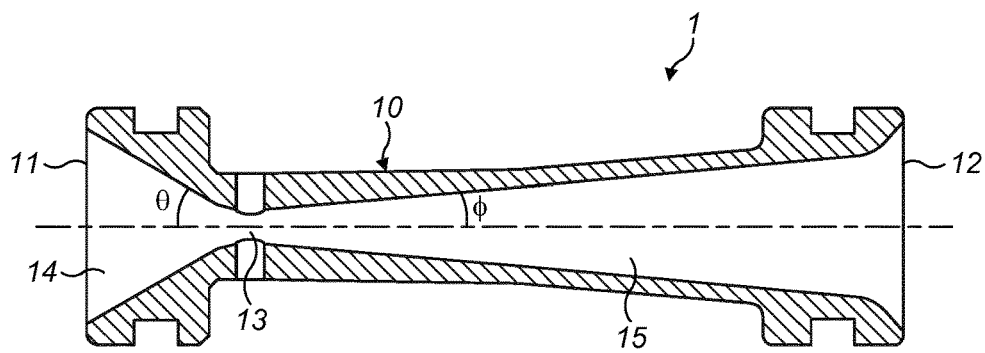
Figure 1C:
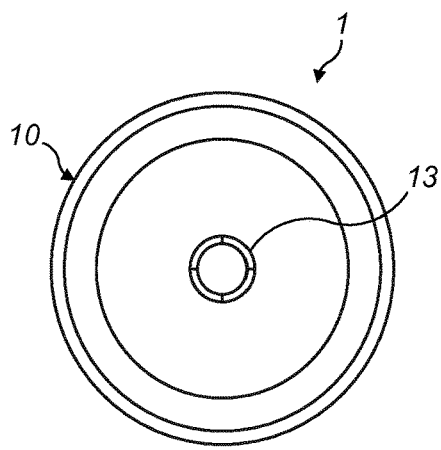

FIG. 1 shows an example of an aerosol guiding device 1 according to the present invention. FIG. 1A shows a schematic view of such an aerosol guiding device 1, FIG. 1B shows a side view of the aerosol guiding device 1 and FIG. 1C shows an end view of the aerosol guiding device 1. In each of FIGS. 1A to 1C, it can be seen that the aerosol guiding device 1 comprises air inlet 11 and air outlet 12 of chamber 10. Aerosol delivery means of an aerosol generating system can be configured such that aerosol is introduced from aerosol generating means of the aerosol generating system into the chamber 10 in use, and an air flow route is defined from the air inlet 11 to the air outlet 12 so as to convey the aerosol to the air outlet 12.

It will be appreciated that any narrative directed to the dimensions of the chamber of the aerosol guiding device in the examples of any of the Figures, for example, the "narrowest part", the "constricted section", the "cross sectional area", the dimensions of the "air inlet" or the "air outlet" are made with reference to the internal dimensions of said chamber.

In FIG. 1, the relative dimensions of the air inlet 11 and the air outlet 12, as well as the relative tapering of the upstream portion 14 and downstream portion 15 of the chamber 10, may be selected to provide pressure control means for controlling the pressure differential between the air inlet 11 and the air outlet 12 of the chamber 10 of the aerosol guiding device 1. In particular, the relative dimensions of the air inlet 11 and the air outlet 12 may also impact on the air flow speed and intensity within the chamber 10.

The air inlet 11 and the air outlet 12 are shown in FIG. 1B to be of the same dimensions. In this case, the pressure differential between said air inlet and said air outlet is substantially zero. Pressure control means may further be provided by the shape of the chamber 10 of the aerosol guiding device 1. The chamber 10 is shown in FIG. 1B to comprise a constricted section 13 of the chamber 10, which is also the narrowest part 13 of the chamber 10. An upstream portion 14 of the chamber 10 is defined between the air inlet 11 and the constricted section 13 and a downstream portion 15 of the chamber 10 is defined between the constricted section 13 and the air outlet 12. Between the air inlet 11 and the narrowest part 13, the dimensions of the cross sectional area of the chamber 10 decreases, and so a pressure drop exists therebetween. Between the narrowest part 13 and the air outlet 12, the dimensions of the cross sectional area of the chamber 10 increases, and so a pressure increase exists therebetween. At the narrowest part 13, there is therefore a region of low pressure. Further, the tapering of the walls of the chamber 10 as shown in FIG. 1B provides pressure control means through the gradual gradients of the tapered walls, which act to reduce drag and therefore homogenise the pressure across a particular cross section of the chamber 10. The pressure drop across the chamber 10 of the aerosol guiding device 1 between the air inlet 11 and the narrowest part 13 may preferably be between 75 and 110 mmWC in use, which is the range of pressure drop across the length of a conventional cigarette.

In alternative embodiments, the air inlet 11 and the air outlet 12 may alternatively have different dimensions, the effects of which will be described below with reference to FIG. 4.

According to the Venturi effect, the narrowest part 13 of the chamber 10 is the point at which air flow through the aerosol guiding means 1 is fastest. By controlling the size and configuration of the narrowest part 13 of the chamber 10, both air flow speed and air flow direction can be regulated, and particle size of the resulting aerosol can be controlled more precisely and in particular reduced relative to known devices. Furthermore, the faster the air flow is in the air flow route in use, the more aerosol can be delivered to the user, thus resulting in a more effective aerosol delivery mechanism and improving both efficiency of an aerosol generating system into which the aerosol guiding means 1 may be inserted and the overall smoking experience for the user.

As shown in FIG. 1B, the upstream portion 14 and the downstream portion 15 of the chamber 10 each taper inwardly from the air inlet 11 and the air outlet 12 respectively towards the narrowest part or constricted section 13 of the chamber 10. The tapering of the chamber 10 advantageously provides improved control of the pressure differential along the air flow route. In particular, the gradual gradients of the tapered portions reduce drag in the chamber 10 and thus regulate air flow in a controlled manner.

The taper angle of the upstream portion 14 of the chamber 10 is shown in FIG. 1B to be larger than the taper angle of the downstream portion 15 of the chamber 10. The length of the upstream portion 14 is also shown to be smaller than the length of the downstream portion 15 of the chamber 10. Thus, air that enters the aerosol guiding device 1 in use will accelerate from the air inlet 11 towards the narrowest part or constricted section 13 and then gradually decelerate from the narrowest part or constricted section 13 towards the air outlet 12, and air flow will be fastest at the narrowest part or constricted section 13.

In FIG. 1B, the taper angle θ of upstream portion 14 is 30 degrees and taper angle φ of downstream portion 15 is 5 degrees. The taper angles have been identified to provide an optimum increase in air flow rate in the chamber 10 at the narrowest part or constricted section 13 resulting in a suitable pressure differential across the chamber 10 of the aerosol guiding device 1 in use. The length of the aerosol guiding device 1 in the example shown in FIG. 1B is 46.5 millimeters, the diameter at its widest part is 13.5 millimeters, the diameter at its narrowest part is 2 millimeters, the length of the upstream portion 14 is 9.25 millimeters and the length of the downstream portion 15 is 37.25 millimeters.

As shown in FIG. 1C, the aerosol guiding device 1 comprises a circular cross sectional shape. As shown in FIG. 1B, the cross sectional shape of the aerosol guiding device 1 decreases from the air inlet 11 to the narrowest part or constricted section 13 and then increases from the narrowest part or constricted section 13 to the air outlet 12. The cross sectional shape of the air inlet 11 and the air outlet 12 are substantially identical such that the pressure differential therebetween is substantially zero.

The aerosol guiding device 1 shown in FIG. 1 can be made for example with a plastic material, which is thermally insulating. Other suitable thermally insulating materials can be used and are known to those skilled in the art. An advantage of this is that when the aerosol guiding device 1 is inserted into an aerosol generating system, the system may be more thermally efficient because heat loss is reduced. This is of particular importance if the aerosol generating means comprises a heater.

Although not shown in FIG. 1, the chamber 10 of the aerosol guiding device 1 may be ribbed internally. Such configuration may advantageously reduce the amount of sheath flow of air along the walls of the chamber, thus improving efficiency of the system.

The chamber 10 of the aerosol guiding device 1 of FIG. 1 may be manufactured using 3D printing technologies. This technique can be used to manufacture a chamber 10 that comprises a single body element, as shown in FIG. 1, which acts to reduce inter component variability. The use of a single element also avoids the need to assemble multiple components, thus increasing the ease of use of the aerosol guiding device 1.

Figure 2A:
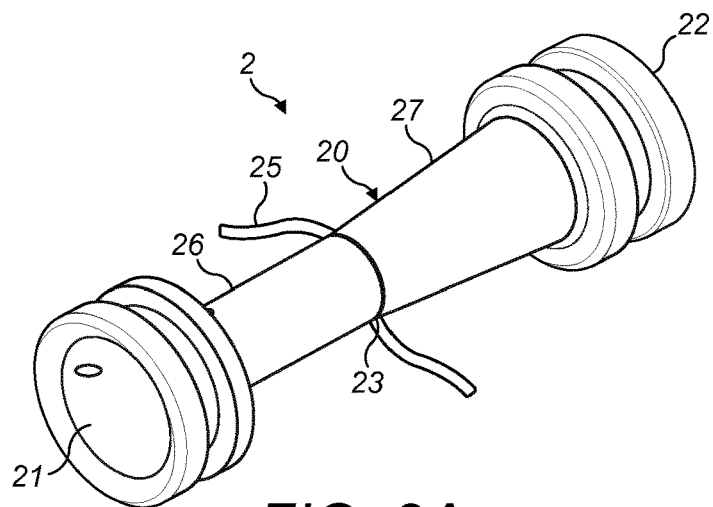
FIGS. 2A to 2C show schematic representations of an aerosol guiding device according to another embodiment of the present invention.
Figure 2B:
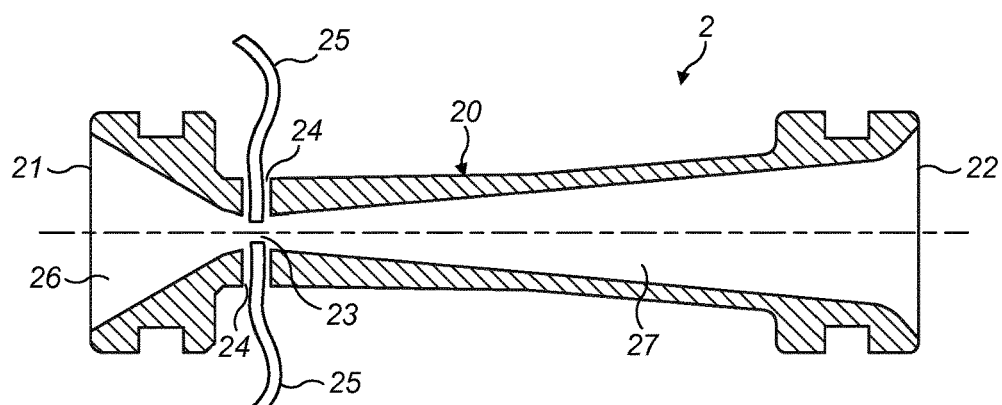
Figure 2C:
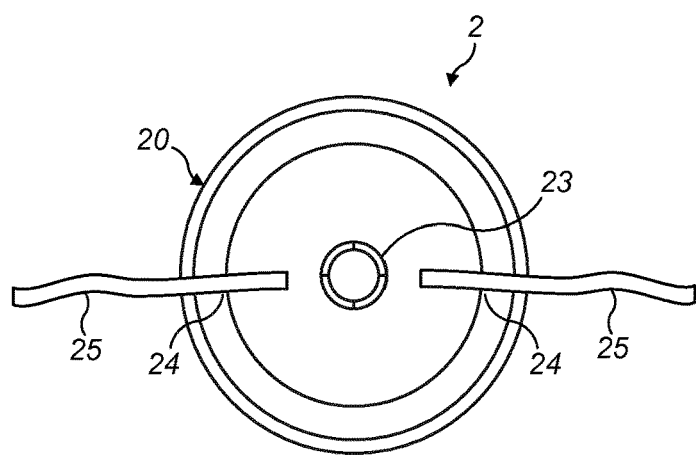

FIGS. 2A to 2C show another embodiment of the aerosol guiding device 2 of the present invention. The aerosol guiding device 2 comprises chamber 20 having air inlet 21 and air outlet 22. Aerosol delivery means of an aerosol generating system can be configured such that aerosol is introduced from aerosol generating means of the aerosol generating system into the chamber 10 in use, and an air flow route is defined from the air inlet 21 to the air outlet 22 so as to convey the aerosol to the air outlet 22. The relative dimensions of the air inlet 21 and the air outlet 22, as well as the relative tapering of the upstream portion 26 and downstream portion 27 of the chamber 20, may be selected to provide pressure control means for controlling the pressure differential between the air inlet 21 and the air outlet 122 of the chamber 20 of the aerosol guiding device 2. In particular, the relative dimensions of the air inlet 21 and the air outlet 22 may also impact on the air flow speed and intensity within the chamber 20.

The air inlet 21 and the air outlet 22 are shown in FIG. 2B to be of the same dimensions. In this case, the pressure differential between said air inlet and said air outlet is substantially zero. Pressure control means may further be provided by the shape of the chamber 10 of the aerosol guiding device 2. The chamber 20 is shown in FIG. 2B to comprise a constricted section 23 of the chamber 20, which is also the narrowest part 23 of the chamber 20. The narrowest part or constricted section 23 of the aerosol guiding means 2 is shown to lie between upstream portion 26 and downstream portion 27 of the chamber 20.

Between the air inlet 21 and the narrowest part 23, the dimensions of the cross sectional area of the chamber 10 decreases, and so a pressure drop exists therebetween. Between the narrowest part 23 and the air outlet 22, the dimensions of the cross sectional area of the chamber 20 increases, and so a pressure increase exists therebetween. At the narrowest part 23, there is therefore a region of low pressure. Further, the tapering of the walls of the chamber 20 as shown in FIG. 2B provides pressure control means through the gradual gradients of the tapered walls, which act to reduce drag and therefore homogenise the pressure across a particular cross section of the chamber 20. The pressure drop across the chamber 20 of the aerosol guiding device 2 between the air inlet 21 and the narrowest part 23 may preferably be between 75 and 110 mmWC in use, which is the range of pressure drop across the length of a conventional cigarette.

All of the features and configuration of said features described with reference to FIG. 1 may also equally apply to the embodiment shown in FIG. 2. Relative to the embodiment shown in FIG. 1, the embodiment shown in FIG. 2 further comprises piercings 24 in the chamber 2 at its narrowest part 23, through which capillary wicks 25 are received. In this embodiment, capillary wicks 25 form part of the aerosol generating means, and piercings 24 form the aerosol delivery means. The capillary wicks 25 may be in connection with a liquid reservoir (not shown) that is located either outside or inside of chamber 20.

In use, when a system comprising the aerosol guiding device 2 is activated, the aerosol generating means, which may further comprise a heater (not shown), vaporises liquid material to form a super saturated vapour. The super saturated vapour mixes with air from at least one air inlet of the system and condenses to form an aerosol, which is delivered to chamber 20 of the aerosol guiding device 2 at its narrowest part 23 via the capillary wicks 25 through piercings 24. By action of suction of the mouth of a user, the aerosol is conveyed towards the air outlet 22 of the chamber 20 of the aerosol guiding device 2 such that an air flow route is defined from the air inlet 21 to the air outlet 22 in a direction from the upstream portion 26 to the downstream portion 27 of the chamber 20.

Referring to FIG. 2B, an area of low pressure is formed at the narrowest part 23 of the chamber 20 so that liquid material is drawn in from a liquid reservoir (not shown). At the same time, the area of low pressure at narrowest part 23 of the chamber 20 causes air flow to increase in speed by virtue of the Venturi effect such that air flow at the narrowest part 23 of the chamber 20 is faster than air flow upstream and downstream of the narrowest part 23.

The liquid to be vaporised may have physical properties that are suitable for use in an aerosol generating system, for example, it may have a boiling point that is suitable for vaporising said liquid at the narrowest part 23 of the chamber 20. If the boiling point of the liquid is too high, then the aerosol generating means will not be able to vaporise said liquid. If the boiling point of the liquid is too low, the liquid may be vaporised even before the aerosol generating means is activated.

The use of a liquid material to be vaporised delivers particular advantages in combination with the delivery of aerosol at the narrowest part 23 of the chamber 20. For example, the area of reduced air pressure at the narrowest point 23 lowers the boiling point of such a liquid, thus making the aerosol guiding device 2 more efficient and saving electrical power. The narrowest part 23 of the chamber 20 may therefore be the aerosol generating means 2 by virtue of its shape. Further, the reduced pressure at the narrowest part 23 of the chamber 20 may act to draw liquid from a liquid reservoir (not shown), via wicks 25, towards the narrowest part 23 of the chamber 20, resulting in better puff-to-puff consistency and ensuring that there is always sufficient liquid to be vaporised, which eliminates the problem of dry puffing. This also results in an increased flow rate of aerosol through the aerosol generating system 2 in use, which will enhance the user experience by providing an increase in aerosol production per puff. This further results in better control over the particle size of the aerosol droplet present in the vaporised liquid as well as control over the spatial distribution of said aerosol particles.

The liquid material may comprise tobacco or flavourants comprising tobacco. In addition or alternatively, the liquid material may comprise flavourants not comprising tobacco. The liquid to be vapourised may also comprise glycerine or glycol derivatives and mixtures thereof.

The aerosol generating means (not shown) may comprise a heater (not shown), wherein the heater comprises any one of a ceramic, a coil of wire, inductive heating means, ultrasonic heating means and/or piezoelectric heating means.

The aerosol generating means (not shown) further comprises a wick 25 that is received by the chamber 20 of the aerosol guiding device 2 at its narrowest part 23 through at least one piecing 24 and the wick 25 is communication with a liquid reservoir (not shown). The aerosol generating system 2 may further comprise said liquid reservoir (not shown). In this example, the aerosol generating means (now shown) may preferably comprise a coil heater that is located at the narrowest part 23 of the chamber 20 or substantially at the narrowest part 23 of the chamber 20. The wicks 25 may draw liquid to be vaporised from at least one liquid reservoir (not shown) located outside of the chamber 20 of the aerosol guiding device, for example.

Figure 3A:
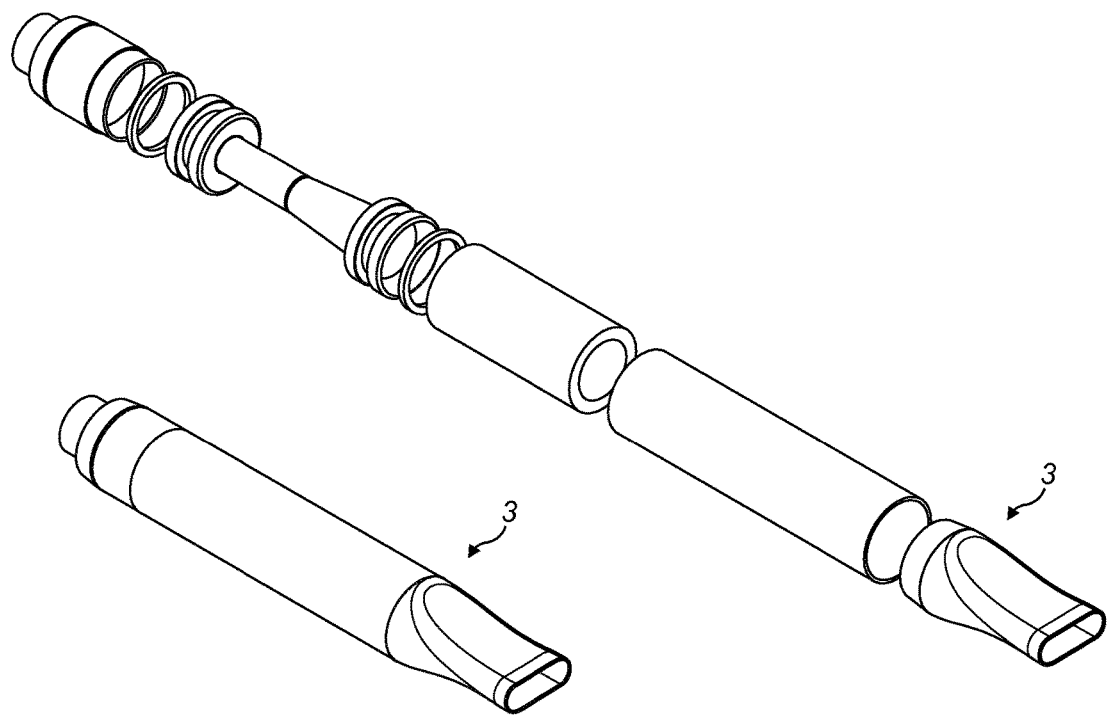
FIGS. 3A to 3C show schematic representations of an aerosol generating system according to an embodiment the present invention.
Figure 3B:
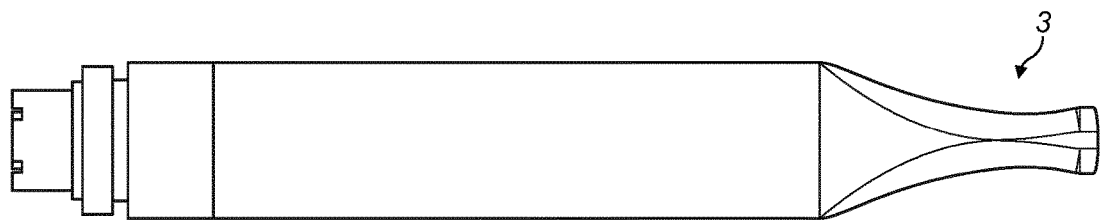
Figure 3C:
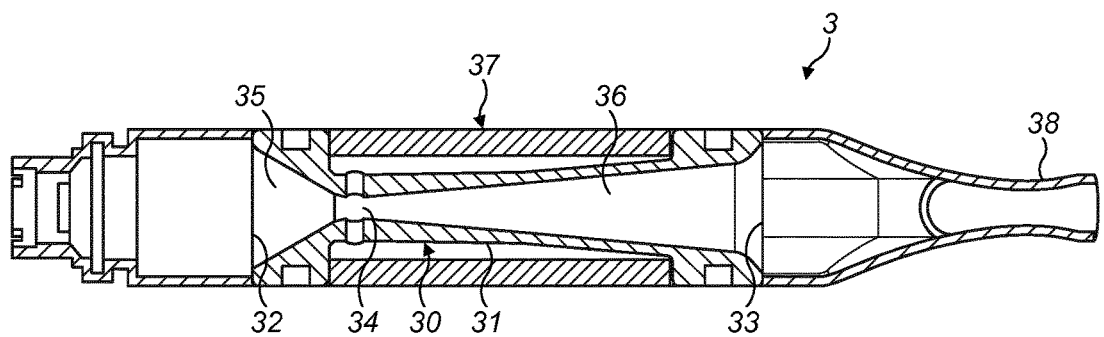

Referring now to FIGS. 3A to 3C, an aerosol generating system 3 is shown. FIG. 3A shows a schematic view and an exploded view of the aerosol generating system 3. FIG. 3B shows a side view of the aerosol generating device 3. FIG. 3C shows a side view of the aerosol generating device 3 in a plane through the centre of the system, wherein the system comprises aerosol generating means (not shown), aerosol delivery means (not shown) and an aerosol guiding device 30, wherein the aerosol guiding device 30 comprises a chamber 31 having an air inlet 32 and an air outlet 33.

The aerosol delivery means (not shown) is configured such that aerosol is introduced from the aerosol generating means into the chamber 31 in use at its narrowest part 34, and an air flow route is defined from the air inlet 32 to the air outlet 33 so as to convey the aerosol to the air outlet 33. The aerosol generating system 3 further comprises an outer shell 37 and a mouthpiece 38. The aerosol guiding means 30 may be either that of the embodiments shown in FIG. 1 or FIG. 2 and having the same pressure control means such that the pressure differential between the air inlet and the air outlet is controlled, or any other suitable aerosol guiding device.

Preferably, the aerosol generating means (not shown) may comprise a wick (not shown) that is received by the chamber 31 of the aerosol guiding device 30 at its narrowest part 34 through at least one piecing (not shown) and the wick (not shown) may be in communication with a liquid reservoir (not shown). The aerosol generating means (not shown) may comprise a coil heater, said coil heater being located at the narrowest part 34 of the chamber 31 or substantially at the narrowest part 34 of the chamber 31. The wick (not shown) may draw liquid to be vaporised from at least one liquid reservoir (not shown) located outside of the chamber 31 of the aerosol guiding device 30, for example.

The outer shell 37 of the aerosol generating system 3 houses the chamber 31 of the aerosol guiding device 30 in use. The outer shell 37 is configured to receive the aerosol guiding device 30, which is insertable and removable from the aerosol generating system 3. This provides particular advantage in that different aerosol guiding devices may be provided for the aerosol generating 3 dependent upon various operational factors. The removable nature of the aerosol guiding device is also advantageous in that said device may be changed should the operational circumstances of the aerosol generating system 3 change over time or an aerosol guiding device reaches the end of its lifetime. The aerosol guiding device may further comprise securing means, for example an O-ring, that secures it to the outer shell 37 of the aerosol generating system 3, which prevents undesired movement of the aerosol guiding device within the aerosol generating system 3 in use. The aerosol guiding device 30 may further provide structural integrity to the aerosol generating system 3.

Figure 4A:
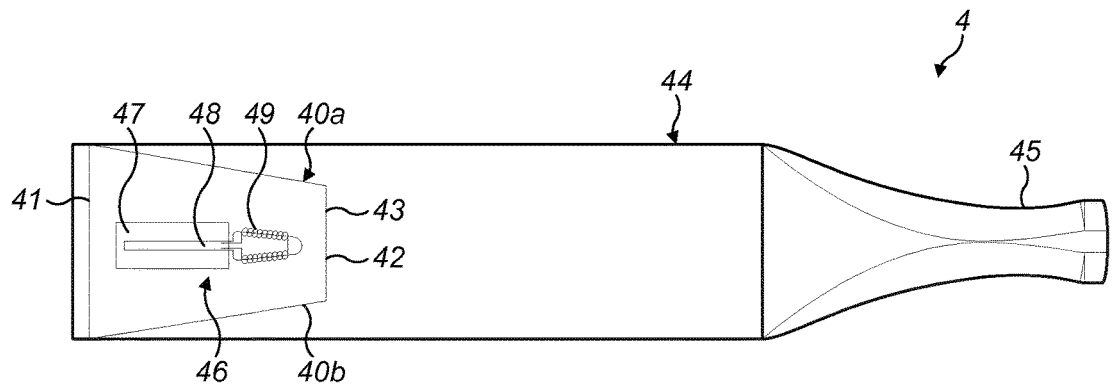
FIGS. 4A to 4C show schematic representations of an aerosol generating system according to another embodiment the present invention.
Figure 4B:
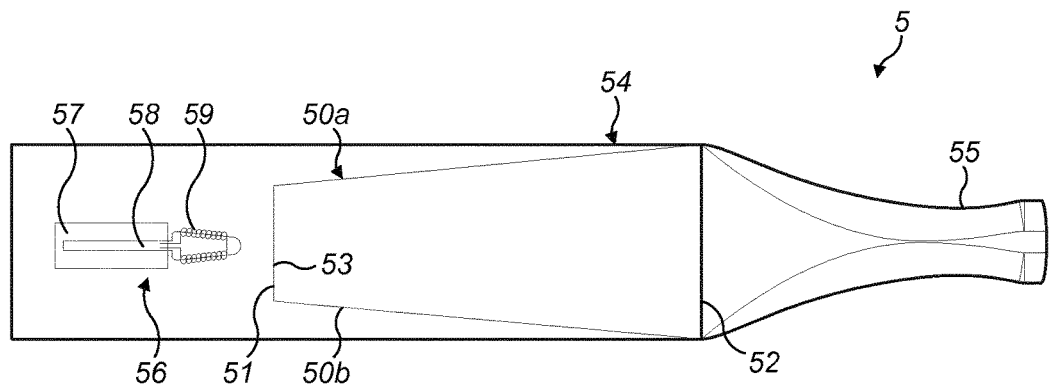
Figure 4C:
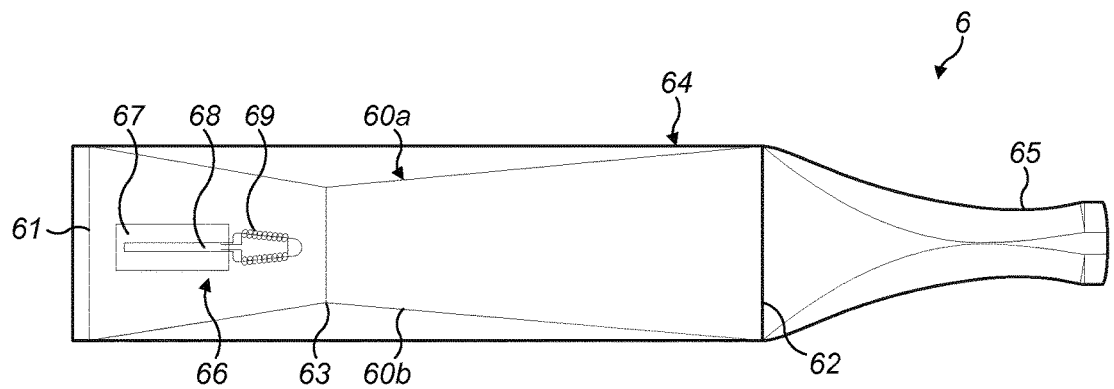

FIGS. 4A to 4C show alternative embodiments of aerosol guiding devices 40a, 50a, 60a, within aerosol generating systems 4, 5, 6. Each aerosol generating system 4, 5, 6 comprises an outer shell 44, 54, 64 and a mouthpiece 45, 55, 65.

In FIG. 4A, the chamber 40b of aerosol guiding device 40a has an air inlet 41 that is of a greater dimension than air outlet 42. By the Venturi effect, air is accelerated from the air inlet 41 towards the air outlet 42, which is also the narrowest part 43 of the chamber 40b. The air may then decelerate after it leaves from the air outlet 42. As can be seen from FIG. 4A, the aerosol generating means 46 comprises liquid reservoir 47, wick 48 and coil heater 49. One end of the wick is in connection with liquid in the liquid reservoir 47 in use and heater 49 heats the other end of wick 48. Wick 48 also acts as the aerosol delivery means as aerosol is generated by the aerosol generating means 46 near the coil of wire heater 49 such that aerosol is introduced to the chamber 40b of the aerosol guiding device 40a at its narrowest part 43.

The aerosol generating means 46 is shown in FIG. 4A to be within the chamber 40b of the aerosol guiding device 40a. Aerosol generating means 46 is also in close proximity to the narrowest part 43 of the chamber 40b. The aerosol generating means 46 may act to regulate air flow in the air flow route by acting as a guide around which the air must flow. In this example, the aerosol generating means may also act as a trap component for trapping larger aerosol particles having a diameter greater than about 1.0 micrometer. This not only removes the larger aerosol particles that may not reach the lungs of a user anyhow, but it also acts to provide better uniformity to the particle size of aerosol particles by removing said larger aerosol particles.

In FIG. 4B, the chamber 50b of aerosol guiding device 50a has an air inlet 51 that is of a smaller dimension than air outlet 52. By the Venturi effect, air is accelerated when it enters the air inlet 51, which is also the narrowest part 53 of the chamber 50b, and decelerated from the air inlet 51 towards the air outlet 52. As can be seen from FIG. 4B, the aerosol generating means 56 comprises liquid reservoir 57, wick 58 and coil heater 59. One end of the wick is in connection with liquid in the liquid reservoir 57 in use and heater 59 heats the other end of wick 58. Wick 58 also acts as the aerosol delivery means as aerosol is generated by the aerosol generating means 56 near the coil of wire heater 59 such that aerosol is introduced to the chamber 50b of the aerosol guiding device 50a at its narrowest part 53.

The aerosol generating means 56 of the aerosol generating system 5 is shown to be located inside the aerosol guiding device 50a. An advantage of locating the aerosol generating means 56 outside the aerosol guiding device 50a is that it will not impact or modify air flow in the chamber 50b of the aerosol guiding device 50a.

It will be appreciated that although aerosol guiding devices 40a, 50a shown respectively in FIGS. 4A and 4B do not extend the full length of the outer shell 44, 54 of the aerosol generating system 4, 5, other embodiments of the present invention may comprise aerosol guiding devices of the same general shape as aerosol guiding devices 40a, 50a that do extend the entire length of the outer shell of the aerosol generating system.

FIG. 4C shows an aerosol guiding device 60a that may be a combination of aerosol guiding devices 40a, 50a as shown in FIGS. 4A and 4B. Alternatively aerosol guiding device 60a may be manufactured from a single element component and not two separate components. An advantage of having an aerosol guiding device 60a comprising a single component is that inter component variability may be reduced in the manufacturing process. Alternatively, the aerosol guiding device 60a could be made of two separate components, for example, aerosol guiding devices 40a, 50a as shown in FIGS. 4A and 4B respectively.

In FIG. 4C, the chamber 60b of aerosol guiding device 60a has an air inlet 61 that is of the same dimensions as air outlet 62. The overall pressure differential between the air inlet 61 and the air outlet 62 is therefore zero. Between the air inlet 61 and the narrowest part 63, the dimensions of the cross sectional area of the chamber 60b decreases, and so a pressure drop exists therebetween. Between the narrowest part 63 and the air outlet 62, the dimensions of the cross sectional area of the chamber 60b increases, and so a pressure increase exists therebetween. At the narrowest part 63, there is therefore a region of low pressure. Further, the tapering of the walls of the chamber 60b as shown in FIG. 4C provides pressure control means through the gradual gradients of the tapered walls, which act to reduce drag and therefore homogenise the pressure across a particular cross section of the chamber 60b. The pressure drop across the chamber 60b of the aerosol guiding device 60a between the air inlet 61 and the narrowest part 63 may preferably be between 75 and 110 mmWC in use, which is the range of pressure drop across the length of a conventional cigarette.

By the Venturi effect, air is accelerated from the air inlet 61 towards the narrowest part 63 of the chamber 60b, and then decelerated from the air inlet 61 towards the air outlet 62. As can be seen from FIG. 4C, the aerosol generating means 66 comprises liquid reservoir 67, wick 68 and coil heater 69. One end of the wick is in connection with liquid in the liquid reservoir 67 in use and heater 69 heats the other end of wick 68. Wick 68 also acts as the aerosol delivery means as aerosol is generated by the aerosol generating means 66 near the coil of wire heater 69 such that aerosol is introduced to the chamber 60b of the aerosol guiding device 60a at its narrowest part 63.

In FIGS. 4A to 4C, each aerosol generating system 4, 5, 6 also comprises a wick 48, 58, 68 and a coil heater 49, 59, 69 that is shown to be close to the narrowest part 43, 53, 63 of the chamber 40b, 50b, 60b. In other examples, the wick 48, 58, 68 and coil heater 49, 59, 69 may extend further towards the narrowest part 43, 53, 63 and/or may extend to a position within the narrowest part 43, 53, 63. This latter arrangement provides for advantageous effects for introducing aerosol into the chamber 40b, 50b, 60b due to the area of low pressure that is formed at the narrowest part 43, 53, 63 by virtue of the Venturi effect. The area of low pressure acts to draw liquid towards the wick 48, 58, 68 and coil heater 49, 59, 69 particularly effectively, thus resulting in more liquid being present at the end of the wick 48, 58, 68 to be vapourised and therefore more aerosol may be delivered to the user per puff.

In each of FIGS. 4A to 4C, the gradual gradients of the tapered portions reduce drag in the chamber and thus regulate air flow in a controlled manner.

It will be appreciated that features described above in relation to one embodiment of the present invention may also equally apply to any other embodiment where appropriate. For example, the aerosol guiding devices 40a, 50a, 60a of FIGS. 4A to 4C respectively may be removable and insertable into the outer shell 37 of aerosol generating system 3 of FIGS. 3A to 3C.

I claim:

1. An aerosol generating system, the system comprising:
aerosol generating means;
aerosol delivery means; and
an aerosol guiding device,
wherein the aerosol guiding device comprises a chamber having an air inlet, an air outlet, an upstream portion that tapers inwardly from the air inlet, and a downstream portion that tapers inwardly from the air outlet, the aerosol delivery means being configured such that aerosol is introduced from the aerosol generating means into the chamber in use, and
wherein an airflow route is defined from the air inlet to the air outlet, and the relative dimensions of the air inlet and the air outlet are selected to provide pressure control means for controlling the pressure differential between the air inlet and the air outlet.

2. The system according to claim 1, wherein the air inlet and the air outlet are of the same dimensions.

3. The system according to claim 1, wherein the taper angle of the upstream portion of the chamber if provided is between 20 and 40 degrees relative to a longitudinal axis of the chamber.

4. The system according to claim 1, wherein the pressure control means is configured to provide a pressure differential between the air inlet and the air outlet of between 75 and 110 mmWC in use.

5. The system according to claim 1, wherein the system further comprises an outer shell for housing the chamber of the aerosol guiding device.

6. The system according to claim 1, wherein the aerosol guiding device is insertable and removable from the aerosol generating system.

7. The system according to claim 1, wherein the aerosol generating means is located outside the device and/or in close proximity to a narrowest part of the chamber.

8. The system according to claim 1, wherein the aerosol generating means comprises a heater, wherein the heater comprises any one of a ceramic, a coil of wire, inductive heating means, ultrasonic heating means, and piezoelectric heating means.

9. The system according to claim 1, wherein the aerosol generating means further comprises a wick that is received by the chamber and the wick is in communication with a liquid reservoir.

10. The system according to claim 1, wherein the air inlet has smaller dimensions than the air outlet or the air inlet has larger dimensions than the air outlet.

11. An aerosol guiding device for use in an aerosol generating system, the device comprising:
a chamber having an air inlet, an air outlet, an upstream portion that tapers inwardly from the air inlet, and a downstream portion that tapers inwardly from the air outlet;
wherein aerosol is introduced from an aerosol generating means into the chamber in use,
wherein an airflow route is defined from the air inlet to the air outlet so as to convey the aerosol to the air outlet, and
wherein the relative dimensions of the air inlet and the air outlet are selected to provide pressure control means for controlling the pressure differential between the air inlet and the air outlet.

12. The device according to claim 11, wherein the air inlet and the air outlet are of the same dimensions.

13. The device according to claim 11, wherein the taper angle of the upstream portion of the chamber is between 20 and 40 degrees relative to a longitudinal axis of the chamber.

14. The device according to claim 11, wherein the pressure control means is configured to provide a pressure differential between the air inlet and the air outlet of between 75 and 110 mmWC in use.

15. The system according to claim 1, wherein the taper angle of the downstream portion of the chamber if provided is between 3 and 7 degrees relative to a longitudinal axis of the chamber.

16. The device according to claim 11, wherein the air inlet has smaller dimensions than the air outlet or the air inlet has larger dimensions than the air outlet.

17. The device according to claim 11, wherein the taper angle of the downstream portion of the chamber is between 3 and 7 degrees relative to a longitudinal axis of the chamber.

* * * * *